US012409241B2

(12) United States Patent
Karitonas et al.

(10) Patent No.: US 12,409,241 B2
(45) Date of Patent: Sep. 9, 2025

(54) UV LIGHT MONITORING SYSTEM FOR A UV DECONTAMINATION APPARATUS

(71) Applicant: Specialist Health Solutions Limited, Kings Lynn (GB)

(72) Inventors: Tautvydas Karitonas, Kings Lynn (GB); Kurt Morgan, Kings Lynn (GB)

(73) Assignee: SPECIALIST HEALTH SOLUTIONS LIMITED (GB)

( * ) Notice: Subject to any disclaimer, the term of this patent is extended or adjusted under 35 U.S.C. 154(b) by 1024 days.

(21) Appl. No.: 17/480,793

(22) Filed: Sep. 21, 2021

(65) Prior Publication Data

US 2022/0088244 A1 Mar. 24, 2022

(30) Foreign Application Priority Data

Sep. 22, 2020 (GB) ...................................... 2014942

(51) Int. Cl.
*A61L 2/10* (2006.01)
*A61L 2/28* (2006.01)

(52) U.S. Cl.
CPC .................. *A61L 2/10* (2013.01); *A61L 2/28* (2013.01); *A61L 2202/25* (2013.01); *A61L 2202/26* (2013.01)

(58) Field of Classification Search
CPC .......... A61L 2/10; A61L 2/28; A61L 2202/25; A61L 2202/26; G01J 1/02; G01J 1/0242; G01J 1/20; G01J 1/429; G01J 2001/4266
See application file for complete search history.

(56) References Cited

U.S. PATENT DOCUMENTS

| 4,082,947 A | 4/1978 | Haywood et al. |
| 9,855,353 B1 | 1/2018 | Stacy |

(Continued)

FOREIGN PATENT DOCUMENTS

| DE | 38 21 743 A1 | 1/1990 |
| EP | 0 047 084 A1 | 3/1982 |

(Continued)

OTHER PUBLICATIONS

Combined Search and Examination Report dated Nov. 23, 2020 issued in corresponding United Kingdom Patent Application No. 2014942.3 (6 pages).

(Continued)

*Primary Examiner* — Timothy C Cleveland
(74) *Attorney, Agent, or Firm* — Barnes & Thornburg LLP; Anusuya Das

(57) ABSTRACT

The invention provides a UV light monitoring system that is capable of estimating the UV irradiance on a target surface oriented at an arbitrary angle relative to a UV emitter that emits UV light. The UV light monitoring system can be used in a system or process for disinfecting a space, where the UV light monitoring system may enable a dose of UV light experienced by a surface in the space to be accurately estimated. The invention can alternatively or additionally provide a mechanism for determining the orientation of a UV light monitor to assist with the optimal placement of the UV light monitor within a space. The orientation is determined based on a comparison between signals received from first and second solar cells that are located on different faces of the UV light monitor.

18 Claims, 6 Drawing Sheets

(56) References Cited

U.S. PATENT DOCUMENTS

| | | |
|---|---|---|
| 2009/0191100 A1 | 7/2009 | Deal |
| 2014/0202521 A1 | 7/2014 | Lee |
| 2015/0086420 A1 | 3/2015 | Trapani |
| 2019/0022263 A1* | 1/2019 | Quilici .................. F21V 21/30 |

FOREIGN PATENT DOCUMENTS

| | | |
|---|---|---|
| WO | 2011/036247 A1 | 3/2011 |
| WO | 2017/153832 A1 | 9/2017 |

OTHER PUBLICATIONS

Search and Examination Report dated Feb. 8, 2021 issued in United Kingdom Patent Application No. 214942.3 (5 pages).

Kohli, Indermeet et al. "UVC Germicidal Units: Determination of Dose Received and Parameters to be Considered for N95 Respirator Decontamination and Reuse." Photochemistry and photobiology vol. 96,5 (2020): 1083-1087. doi:10.1111/php.13322.

European Search Report dated Feb. 9, 2022 issued in corresponding Patent Application No. 21198342.4 (12 pages).

Przybyla, "Understanding UV light measurement Part1 The irradiance measurement", Apr. 23, 2020 (6 pgs).

\* cited by examiner

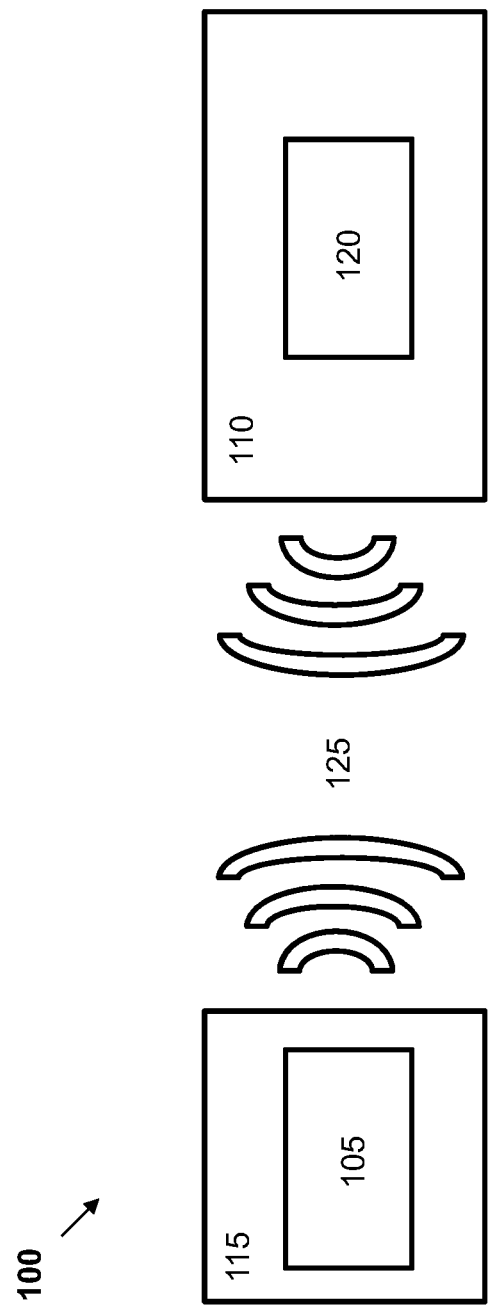

Fig. 5
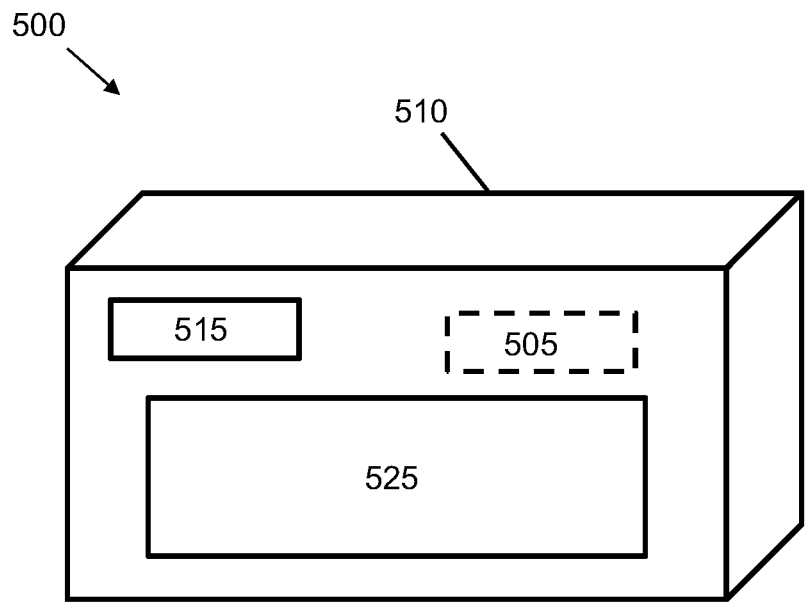
Fig. 5A
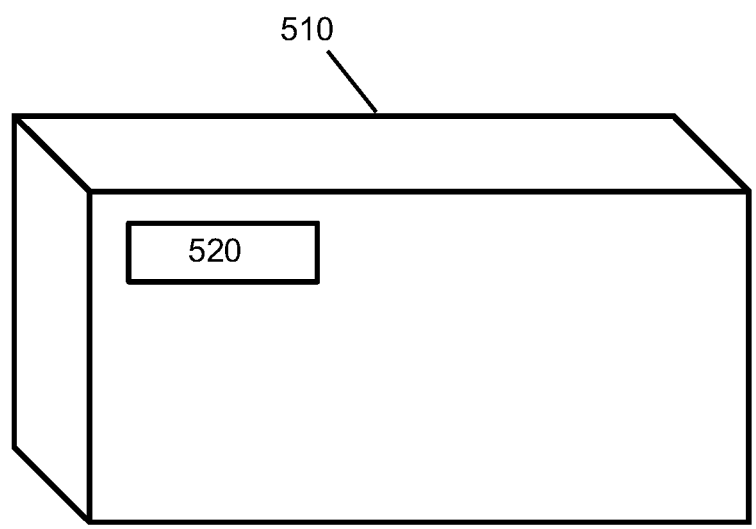
Fig. 5B

UV LIGHT MONITORING SYSTEM FOR A UV DECONTAMINATION APPARATUS

CROSS-REFERENCE TO RELATED APPLICATIONS

This application claims priority to United Kingdom Patent Application No. 2014942.3, entitled "UV LIGHT MONITORING SYSTEM FOR A UV DECONTAMINATION APPARATUS" filed on Sep. 22, 2020, the contents of which is expressly incorporated by reference herein in its entirety.

FIELD OF THE INVENTION

This invention relates generally to systems for measuring UV light, and more particularly to UV light measuring systems that are capable of estimating UV irradiance on a target surface. The invention also relates to use of such systems in the context of disinfection of a space using UV light.

BACKGROUND

UV light monitors are able to detect an amount of UV light, or irradiance, falling on a particular area in order to produce a UV irradiance measurement. A common context in which this information is desired is UV light safety systems that are designed to ensure that a user experiences less than the maximum dose of UV irradiance. In this context a UV light monitor is designed to measure a maximum 'overkill' dose to ensure that the 'worst case' dose is being measured. For this reason it is very likely in such systems that the actual dose is being overestimated, particularly in the case of surfaces that are not exposed to the full intensity of the UV light source. This is acceptable from a safety perspective but is not useful in contexts where an accurate estimate of the actual dose received by a surface is sought.

Another situation in which it is useful to know an actual UV irradiance is the disinfection of a space, e.g. a room in a hospital, or the interior of an emergency services vehicle, and/or specific objects within such spaces like a bed, trolley, stretcher, gurney, table, chair, etc.

In this type of UV disinfection system a maximum dose calculation as used in a safety system is of very little use because this would lead to overestimation of the dose received by the vast majority, if not all, of the surfaces being disinfected. Surfaces that have not received the requisite dose of UV will not be properly disinfected but may be considered disinfected, which is clearly undesirable. Instead, in UV disinfection systems what is needed is an estimate of the actual UV dose received by a target surface. The estimate should be as accurate as possible. This allows validation of the UV disinfection process so that it can be stated with confidence that the target surface has been disinfected to the required level.

The disinfection efficacy of a UV disinfection process can be quantified by determining the proportion of target pathogens that are resident on the surface before disinfection begins which are killed or otherwise disabled by the disinfection process. This may be expressed in the form of a logarithmic reduction. It is often desirable to be able to guarantee that a UV disinfection process provides a particular level of disinfection efficacy, e.g. a log 4, log 5, or log 6 reduction.

The disinfection efficacy depends on the UV dose received by a surface, where the dose is equal to the UV irradiance summed over the total time that the surface is exposed to UV light. Traditionally when seeking to achieve a particular level of disinfection efficacy there has been a tendency to over-expose the target surface to UV light, the rationale being that this 'overkill' approach is highly likely to provide the required level of disinfection efficacy.

However, overexposing the target surface is not an ideal solution for several reasons.

Firstly, even if an overkill dose is sought it is not necessarily achieved in practice for all surfaces being disinfected. That is, some surfaces may still be underexposed even when it is thought that an overkill approach is being taken. This is highly undesirable because it can lead to a surface being considered as disinfected to a certain level where in fact it has not been. Validation of the disinfection process is therefore desirable to ensure that a surface has indeed received sufficient UV light to kill or otherwise disable target pathogens such that confidence in the disinfection process is high.

Some existing UV disinfection systems do not make use of any validation techniques whatsoever, leaving open the risk that surfaces which are considered to have been disinfected to a certain level have in fact not been. Other disinfection systems measure the UV light reflected from a target surface to estimate the actual dose received at the target surface and validate in this way. While this may work to some extent, dosage estimates tend to be relatively inaccurate such that the confidence in the disinfection process may still not be particularly high. Still other UV disinfection systems place UV sensors in the space to be disinfected—while this improves the UV dose estimate accuracy and disinfection process confidence, it is not possible to cover the entire space in sensors meaning that this technique is limited to validation of disinfection of only those surfaces that have a sensor placed on them.

Secondly, some materials such as plastic are sensitive to UV light and can degrade under UV light. Overexposure therefore promotes more rapid degradation of these materials which is clearly undesirable.

Thirdly, a large proportion of the UV wavelength band is harmful to human and/or animal tissue and therefore it is necessary to prevent a space from being occupied by people and/or animals while the space is being disinfected. This often prevents the space from being used for its primary purpose, e.g. a hospital room or emergency services vehicle cannot accommodate patients and/or staff while the disinfection process is occurring. Overexposure of UV light leads to a longer treatment time than strictly necessary to achieve the desired level of pathogen reduction, preventing the space from being used for its primary purpose for longer than is actually needed. This is also undesirable.

What is needed is a technique for validating the efficacy of a UV disinfection process to a high level of confidence for any arbitrary surface within the space being disinfected. The validation technique should be reliable and represent what actually happens during the disinfection process.

Many UV disinfection systems include one or more UV emitters which generate UV light. The emitter(s) may be mobile. It will be appreciated that the position of an emitter within a space will affect the irradiance incident on a given target surface within the space. One parameter that affects the irradiance is the distance between the emitter and the target surface. It is therefore important that a mobile UV emitter is correctly placed relative to a target surface when seeking to obtain a particular level of pathogen reduction.

Placing the emitter too far away from the target surface can lead to underexposure and a corresponding failure to achieve the desired disinfection efficacy, whereas placing the emitter too close can lead to overexposure that lengthens treatment times unnecessarily and may also damage UV-sensitive materials more than necessary. This complicates placement of a mobile UV emitter and tends to lead to such placement having to be performed by a specially trained operator.

UV emitters tend to emit UV light in an intensity distribution that varies as a function of angle. In some cases such as a UV-emitting LED this is an inherent property of the UV emitting component itself. Additionally the mechanical structure of the UV emitter that houses the UV emitting component is typically opaque to UV light, resulting in blockage of the UV light over some angles. A further complication arises from the fact that one target surface within in a space tends to be oriented at a different angle relative to the UV emitter to a second target surface within a space. The combination of these factors makes it difficult to ensure that an arbitrarily oriented surface receives a UV dose appropriate for achieving the desired level of pathogen reduction. Typically this issue has again been dealt with by adopting an overkill approach by overexposing surfaces to ensure that they receive at least the required dose of UV light, to the detriment of treatment cycle time and UV-sensitive material degradation.

It will be apparent from the above that there is a need in the art to provide techniques that enable more precise disinfection of target surface(s) within a space such that traditional overkill techniques are no longer required.

SUMMARY OF THE INVENTION

Broadly speaking the invention provides a UV light monitoring system that is capable of estimating the UV irradiance on a target surface oriented at an arbitrary angle relative to a UV emitter that emits UV light. The UV light monitoring system can be used in a system or process for disinfecting a space, where the UV light monitoring system may enable an actual dose of UV light experienced by a surface in the space to be accurately estimated. This enables the disinfection process to be validated to a high confidence level. The treatment time can also be correspondingly selected such that overexposure is not needed. The invention can alternatively or additionally provide a mechanism for determining the orientation of a UV light monitor to assist with the optimal placement of the UV light monitor within a space. The orientation is determined based on a comparison between signals received from first and second solar cells that are located on different faces of the UV light monitor. Feedback can be provided to assist an operator seeking to place the UV light monitor correctly in the space.

In a first aspect the invention provides a UV light monitoring system comprising a processor and a UV light monitor including a UV sensor, wherein the UV light monitoring system is configured to calculate a UV irradiance on a target surface that is remote from the UV light monitor based on UV light intensity measurements made by the UV light monitor and an angle between the UV sensor and the target surface.

In a second aspect the invention provides a system for disinfecting a space, the system comprising the UV light monitoring system of the first aspect and a UV emitter, wherein the system is configured to determine a disinfection cycle time for the target surface based on the calculated UV irradiance.

In a third aspect the invention provides a method of disinfecting a target surface within a space, the method comprising: positioning a UV emitter in the space; positioning a UV light monitor on a first surface within the space, the first surface being different from the target surface; activating the UV emitter to cause the emission of UV light; measuring a UV irradiance of the first surface using the UV light monitor; calculating a UV irradiance on the target surface based on the measured UV irradiance; determining a disinfection cycle time for the target surface based on the calculated UV irradiance; and exposing the target surface to UV light from the UV emitter for a duration equal to the disinfection cycle time.

In a fourth aspect the invention provides a UV light monitoring system comprising a processor and a UV light monitor, the UV light monitor including a UV sensor, a first solar cell and a second solar cell, wherein the first and second solar cells are located on different faces of the UV light monitor, and wherein the UV light monitoring system is configured to determine: i) an orientation of the UV light monitor based upon a comparison between a parameter of the first solar cell and a parameter of the second solar cell; and ii) a UV irradiance incident upon a target surface based on measurements made by the UV sensor.

Optional features of the invention are set out in the appended dependent claims.

BRIEF DESCRIPTION OF DRAWINGS

The invention is described with reference to the following figures which illustrate, by way of example only, particular embodiments of the invention.

FIG. 1 shows a UV light monitoring system according to an embodiment of the invention;

FIG. 5A shows a front view of a UV light monitoring system according to a further embodiment of the invention;

FIG. 5B shows a rear view of a UV light monitoring system according to the further embodiment of the invention.

DETAILED DESCRIPTION

Figure 2B:
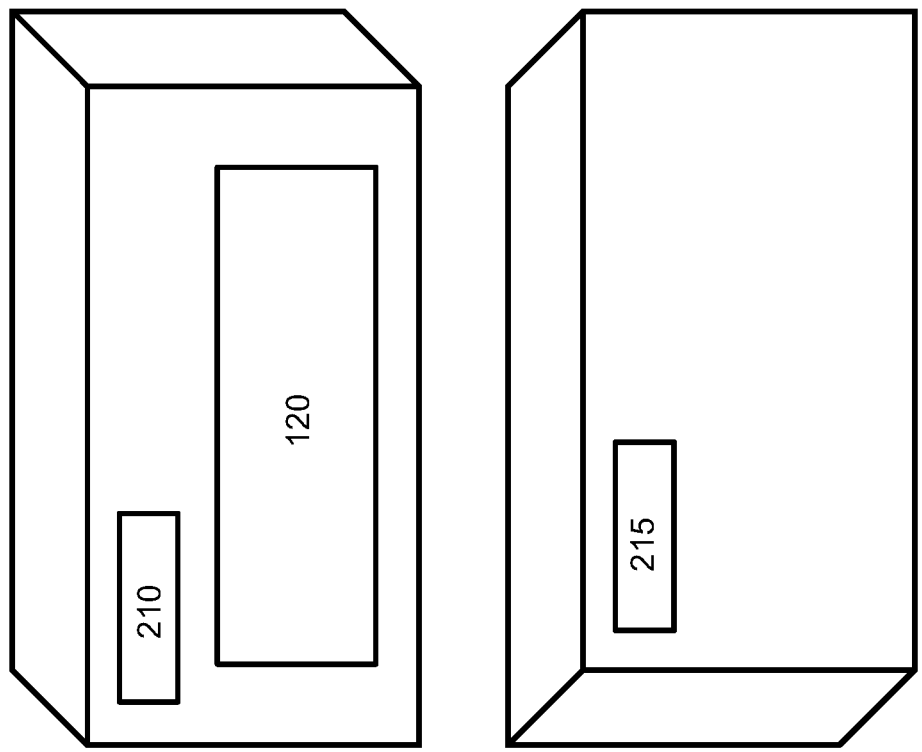
FIGS. 2A and 2B each show different example arrangements of a UV light monitor that is suitable for use in the system of FIG. 1.

The following terms used within this specification should be understood as follows:

UV: Electromagnetic radiation having a wavelength residing within the ultraviolet wavelength range. This wavelength range is typically taken to be approximately 100 nm to approximately 400 nm. This wavelength range is sometimes subdivided into UV-A, UV-B and UV-C bands, and the term UV encompasses light residing in any one or more of these wavelength bands.

Target surface: a surface on which is it is desired to estimate a UV irradiance. Examples of target surfaces include: a part or all of a floor of a room, a part or all of a wall of a room, a face of an object within a room such as an upper face, side face, end face or lower face of a bed, chair, trolley, gurney, etc. It will thus be understood that a single object or face of an object can comprise multiple target surfaces, e.g. an upper portion and lower portion of a wall can each be distinct target surfaces, or the various different faces of a bed can each be distinct target surfaces. Typically but not exclusively a target surface is defined such that UV irradiance from a given UV emitter does not vary significantly over the area of the target surface, e.g. UV irradiance is uniform or substantially uniform over the entire target surface, e.g. varying less than 15%, or less than 10%, or less than 5% across the entire target surface. A target surface may be planar or substantially planar.

Irradiance: the power received by a surface per unit area, as can be measured in units of watts per square centimeter. In the case of a UV irradiance this value can optionally be corrected for background UV light, e.g. as generated by the sun or some other local source of UV light.

Dose: the total irradiance received by a surface over a given time, as can be measured in units of joules per square centimeter.

UV emitter: a device capable of emitting UV light. A UV emitter can include one or more UV light generating components. Broadband and narrowband UV emitters are within the scope of the invention.

Disinfection: the process by which one or more species of pathogenic microorganism are disabled, killed, rendered inert or otherwise affected in a way that significantly reduces if not entirely eliminates their ability to cause disease in the human and/or animal body. Examples of pathogenic organisms that can be disabled, killed etc. by the present invention include *Staphylococcus*, COVID-19, *C. difficile* and others.

Disinfection level: a quantification of the efficacy of a disinfection process. This may be measured according to the logarithm reduction scale as defined by the Environmental Protection Agency of the USA.

Furniture: this term is understood broadly to refer to an object within a space that is not part of the structure of the space itself, i.e. not a wall, ceiling, etc. Examples of furniture include: a bed, a table, a chair, a desk, a trolley, a cabinet, a curtain, a door, a shower, a bath, a gurney, and the like.

Having provided the foregoing definitions, the invention is described below with reference to the Figures.

FIG. 1 shows a UV light monitoring system 100 according to an embodiment of the invention. System 100 includes a processor 105, a UV light monitor 110 and optionally also includes a disinfection process controller 115 that is configured to control a disinfection process.

Processor 105 can be any type of processor, e.g. a microprocessor, a microcontroller or a programmable logic controller (PLC). In FIG. 1 processor 105 is shown as a component within the disinfection process controller 115. Alternatively, processor 105 can be integrated within UV light monitor 110, in which case process controller 115 can be omitted from system 100. Processor 105 may also represent distributed computing capabilities, e.g. a microprocessor located within UV light monitor 110 and a central processing unit located within controller 115.

UV light monitor 110 is a device that is capable of measuring a UV irradiance. To enable UV light measurements UV light monitor 110 includes a sensor 120 that is capable of detecting UV light and producing a signal that is indicative of the detected UV irradiance. Sensor 120 may be, for example, a UV phototube or a charge-coupled device that is sensitive to UV light. The invention is not limited in this respect and any component capable of detecting UV light and producing a signal from which an irradiance can be derived is suitable for use as sensor 120. It will also be appreciated that sensor 120 can be a composite structure that is formed of multiple individual sensors. It will additionally be appreciated that UV light monitor 110 can include multiple sensors like sensor 120.

UV light monitor 110 is preferably a portable device such that it can be moved around in a space. In this regard UV light monitor 110 may be a handheld device approximately the size and shape of well-known portable electronic devices such as a mobile telephone, a tablet computer, and the like. The invention is however not limited in this regard and UV light monitor 110 can take any desired form.

UV light monitor 110 preferably includes one or more communication interfaces (not shown), e.g. a Bluetooth™ antenna, a WiFi antenna, a cellular radio, a low-power wide-area-network (LPWAN), etc. The communication interface(s) may be used to enable UV light monitor 110 to transmit and receive data and/or control signals to and from other components of system 100, e.g. disinfection process controller 115, other UV light monitors and/or a UV emitter. The design, configuration and function of such communication interfaces is known per se and so is not described in detail here.

If present, disinfection process controller 115 also preferably includes one or more communication interfaces (not shown) of the type discussed in the paragraph directly above. This enables two way wireless communication 125 between UV light monitor 110 and disinfection process controller 115, e.g. to send and/or receive data and control signals. Controller 115 may additionally or alternatively be in communication with a UV emitter that generates UV light. More detail is provided on this later in this specification.

It will be appreciated that system 100 can include multiple UV light monitors that are each like UV light monitor 110. Each such monitor can be in communication with disinfection process controller 115, if present, and/or any one or more of the other UV light monitors (e.g. in a Bluetooth™ piconet).

UV light monitoring system 100 is configured to calculate a UV irradiance on a target surface that is remote from UV light monitor 110 based on UV light irradiance measurements made by the UV light monitor and an angle between a plane of the UV sensor and a plane of the target surface. Advantageously this means that UV light monitor 110 does not have to be oriented at the same angle relative to a UV emitter as the target surface in order to provide an accurate estimate of the UV irradiance at the target surface.

Here, 'remote' does not require there to be significant distance separating the UV light monitor and the target surface. Rather, the target surface is remote in the sense that the UV irradiance at the target surface is expected to differ by a non-trivial amount from the UV irradiance at the UV light monitor. Put another way, it is not valid to assume that the UV irradiance measured by the UV light monitor is equal to, or approximately equal to, the UV irradiance at the target surface. It will be appreciated that in fact the target surface can be physically very close to the UV light monitor and this be true; for example, a UV emitter that directs UV light in a vertical direction can produce a significantly different UV irradiance on a horizontal floor compared with a vertical wall that is adjacent the floor.

Figure 6:
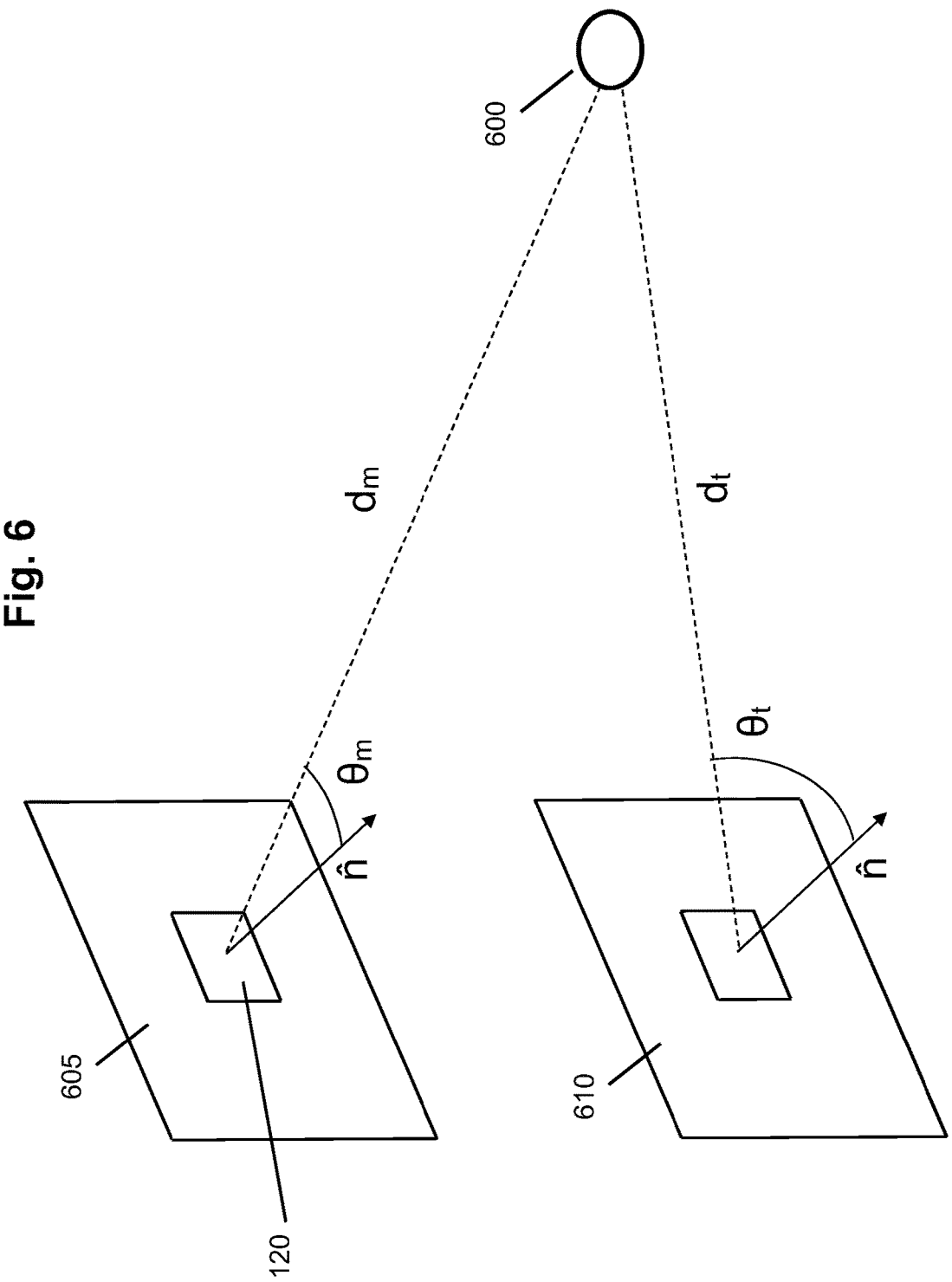
FIG. 6 is a diagram to assist in the understanding of certain calculations that can be performed in accordance with the invention.

Referring here to FIG. 6, a UV emitter 600 is positioned relative to sensor 120 that is located on a first surface 605. UV light emitted by emitter 600 (shown in dashed line in FIG. 6) forms an angle $\theta_m$ relative to the normal ($\hat{n}$) of the plane of sensor 120. UV light emitted by emitter 600 also forms an angle $\theta_1$ relative to the normal of target surface 610. Sensor 120 is located a distance $d_m$ from emitter 600 and target surface 610 is located a distance $d_t$ from emitter 600. In this configuration, one way in which the UV irradiance on the target surface can be calculated is by using equation [1] below:

$$I_t = I_m \left(\frac{d_m}{d_t}\right)^2 \frac{\cos \theta_t}{\cos \theta_m} \quad [1]$$

where $I_m$ is the irradiance measured by sensor 120, $I_t$ is the irradiance calculated for the target surface, the other terms of this equation being as defined above. In the case where either the sensor or the target surface is made up of multiple regions of different orientation, the major region(s) by area may be taken as representative of the plane of the sensor or target surface.

$\theta_m$ and $\theta_t$ may be measured using a suitable instrument such as an angle meter, digital angle measure or digital protractor. Alternatively UV light monitor 110 may include an angle meter or similar as part of its structure such that UV light monitor 110 can be placed on the target surface to enable these angles to be measured directly. These measurements would take place in advance of a disinfection process being performed, i.e. before a UV emitter is turned on. Measurements may be stored in a memory that is accessible to processor 105 in association with a list of target surfaces such that the angle between the UV light monitor and the target surface may only need to be measured once for target surfaces that are fixed.

In the case where UV light monitor 110 includes multiple UV light sensors, if the sensors are oriented at different angles it may be advantageous to perform the irradiance calculation using equation [1] for the target surface based on the irradiance measured by the one of the multiple sensors that is oriented most similarly to the target surface, i.e. the one of the multiple sensors for which the value of $\theta_m$ is closest to the value of $\theta_t$. The same is true for a UV light monitor 110 that includes UV light sensor(s) that are capable of providing a signal that is usable to determine UV irradiance as a function of the angle of incidence of UV light upon sensor 120. In this case the irradiance at the value of $\theta_m$ that is closest to the value of $\theta_t$ may be used in equation [1] for $I_m$. In either of the above cases, extrapolation and/or interpolation of the UV irradiance as measured by sensor 120 may be performed to better estimate UV irradiance at the angle corresponding to that of the target surface.

Processor 105 may perform the calculation based on raw measurements made by sensor 120, or some pre-processing may be performed before the UV irradiance is calculated. One example of pre-processing is the subtraction of ambient UV light irradiance from the UV irradiance measured by sensor 120. This can be performed by taking a background UV irradiance measurement in the absence of a UV emitter, or with a UV emitter present but turned off. The ambient irradiance can be stored in a memory within system 100, e.g. as part of UV light monitor 110 and/or disinfection process controller 115 (if present) for subtraction from the UV irradiance measured by sensor 120. This can advantageously improve the accuracy of UV irradiance calculations made by system 100.

In the case where background UV irradiance is taken into account, equation [1] can replaced with equation [2] below:

$$I_t = (I_m - I_A) \left(\frac{d_m}{d_t}\right)^2 \frac{\cos \theta_t}{\cos \theta_m} \quad [2]$$

where $I_A$ is the ambient irradiance as measured by sensor 120.

UV light monitor 110 may include a distance measuring component that is configured to measure the distances $d_m$ and/or $d_t$. The distance measuring component can be based on any currently known or future developed technique for measuring distances, such as: a time of flight or reflected light intensity distance measuring component, an ultrasonic measuring component, a laser measuring component, and/or a mechanical measuring component. Such techniques are known per se and so are not described in detail here. Alternatively, the distances $d_m$ and/or $d_t$ can be measured using a similar distance measuring component that is separate from UV light monitor 110.

As a further alternative, in cases where multiple sensors like sensor 120 are present, $d_m$ can inferred from UV irradiance measurements made by the sensors. For example, the multiple irradiance measurements can be combined to calculate the position of the UV light emitter which would result in the measured irradiances on the various sensors. In this case the distance measuring component can be the sensor 120 itself.

UV light monitor 110 can include a reference distance measuring component that is configured to measure a distance from the UV light monitor to a reference surface. This assists with the correct positioning of UV light monitor 110 within a space. The reference surface may be the same as the target surface, or different. The reference distance measuring component may be the same component as the distance measuring component described above, if one is present, or a different component. The reference distance measuring component can be based on any currently known or future developed technique for measuring distances, such as: a time of flight or reflected light intensity distance measuring component, an ultrasonic measuring component, a laser measuring component, and/or a mechanical measuring component. Such techniques are known per se and so are not described in detail here.

In conjunction with the reference distance measuring component, UV light monitor 110 can also include a position alert component. The position alert component is configured to alert an operator when the position of UV light monitor 110 relative to the reference surface is suboptimal. The position alert component can be any component capable of alerting an operator, including any combination of: one or more lights such as LEDs, one or more loudspeakers, and the like.

Processor 105 can be configured to use distance measurements made by the reference distance measuring component to determine the current position of UV light monitor 110 within a space relative to the reference surface. The reference surface could be, for example, a wall of a room or a face of a UV emitter. Processor 105 may have access to a memory storing an optimal distance for UV light monitor 110 to be spaced from the reference surface, and processor 105 may be configured to trigger the position alert component when the distance from the UV light monitor to a reference surface is not equal to the optimal distance, or not within a threshold value from the optimal distance. This can advantageously alert an operator to incorrect placement of UV light monitor 110, e.g. too close to a UV emitter such that UV irradiance is overestimated, or too close to a wall such that UV irradiance is underestimated. This may simplify the deployment of UV light monitor 110 such that it can be correctly placed by an operator that has not undergone specific training.

UV light monitor 110 may include one or more solar cells. Solar cells per se are known and therefore are not described in detail here. As is known per se, solar cells can be used to generate electrical power for powering electronics within UV light monitor 110, e.g. processor 115, sensor 120 and/or the aforementioned communication interface(s). UV light monitor 110 may include a rechargeable battery that is electrically coupled to the solar cell(s). Any known or future developed solar cell can be used.

In addition to providing electrical power, the solar cell(s) can advantageously be used as a proximity detection mechanism. Specifically, by monitoring a parameter of the solar cell(s), it is possible to determine the proximity of the UV light monitor to a UV emitter. The monitored parameter may be electrical current, voltage and/or power generated by the solar cell(s), or any other parameter that is expected to vary in a predictable manner as a function of distance from the UV emitter. UV light monitor 110 can include a proximity alert component that is capable of alerting an operator, including any combination of: one or more lights such as LEDs, one or more loudspeakers, and the like. Processor 105 may be configured to enable the proximity alert component when the parameter of the solar cell(s) exceeds a threshold value, this being an indication that UV light monitor 110 is too close to the UV emitter. This can advantageously assist an operator who has not had specific training in the optimal positioning of UV light monitor 110. Additionally, since the solar cell(s) is/are principally for providing power for the UV light monitor, making use of the solar cell(s) as a proximity detector can provide an advantageous additional function without significantly increasing the complexity and cost of the UV light monitor.

Processor 105 may be configured to record the position of UV light monitor 110 as determined by any of the techniques discussed above in a log file stored in a memory, preferably a non-volatile memory. The log file may be useful in demonstrating compliance with a particular disinfection procedure.

Figure 2A:
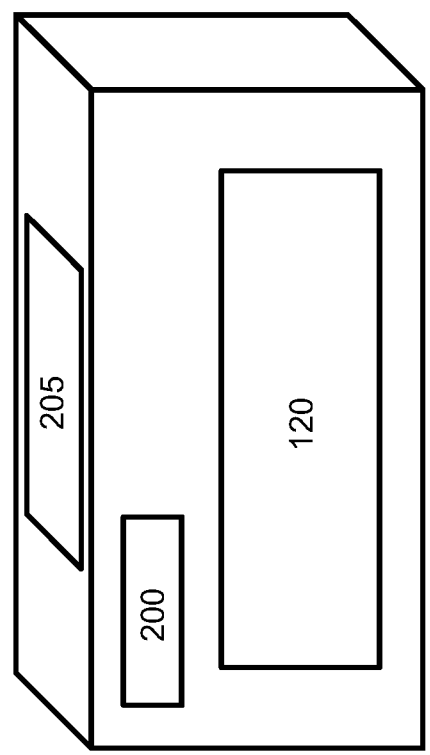

UV light monitor 110 may include at least first and second solar cells that are located on different faces of the UV light monitor. Two example arrangements of such a UV light monitor are shown in FIGS. 2A and 2B. In each case UV light monitor 110 is approximately cuboidal, e.g. of a similar shape to a mobile telephone or tablet computer.

In FIG. 2A the first solar cell 200 is located on a front face of the UV light monitor, this being the same face as the face on which sensor 120 is located. The second solar cell 205 is located on an upper face of the UV light monitor. As can be seen from the figure, this results in a 90 degree angle between the plane of first solar cell 200 and second solar cell 205. This tends to cause a detectable difference in a parameter of the first solar cell compared with the same parameter of the second solar cell, e.g. an electrical current, voltage and/or power of the first solar cell compared with an electrical current, voltage and/or power of the second solar cell.

FIG. 2B shows in the upper portion a front view of UV light monitor 110 and in the lower portion a rear view of UV light monitor 110. As can be seen the first solar cell 210 is located on a front face of the UV light monitor and the second solar cell 215 is located on a rear face of the UV light monitor, i.e. the faces are opposite one another. In this configuration typically one of the solar cells will be shadowed by the body of the UV light monitor and this tends to cause a detectable difference in a parameter of the first solar cell compared with the same parameter of the second solar cell, e.g. an electrical current, voltage and/or power of the first solar cell compared with an electrical current, voltage and/or power of the second solar cell.

It will be appreciated that the positions of the first and second solar cells as shown in FIGS. 2A and 2B are purely exemplary and can therefore be varied without departing from the scope of the invention. Preferably the positions of the first and second solar cells are selected such that it is expected that one of more of the aforementioned parameters will be detectably different for the first solar cell compared with the same parameter for the second solar cell. One solar cell may be located on a face of the UV light monitor that includes sensor 120 and the other solar cell may be located on a different face of the UV light monitor that does not include sensor 120.

Processor 105 can be configured to determine an orientation of the UV light monitor based upon a comparison between one or more of the aforementioned parameters of the first solar cell and the same parameter(s) of the second solar cell. The orientation may be determined relative to a UV light emitter, or relative to some other reference such as gravity.

While only two solar cells have been shown in FIGS. 2A and 2B, it will be appreciated that the techniques discussed in connection with these figures can be extended to any number of solar cells, e.g. three, four, or more solar cells each located on a different face of the UV light monitor.

UV light monitor 110 may include an orientation alert component. The orientation alert component can be any component capable of alerting an operator, including any combination of: one or more lights such as LEDs, one or more loudspeakers, and the like. The UV light monitor may be configured to activate the orientation alert component based upon a comparison between the determined orientation and a reference orientation. The reference orientation may specify an optimal orientation for UV light monitor 110. In this way an operator that has not received specialist training can be assisted in the placement of the UV light monitor and prevented from placing the monitor in a sub-optimal orientation, e.g. in an orientation that significantly or totally prevents sensor 120 from detecting UV light such as front face down in the configuration of FIG. 2A or 2B. Moreover, since the solar cells are principally for providing power for the UV light monitor, making use of the solar cells as an orientation detector can provide an advantageous additional function without significantly increasing the complexity and cost of the UV light monitor.

Figure 3:
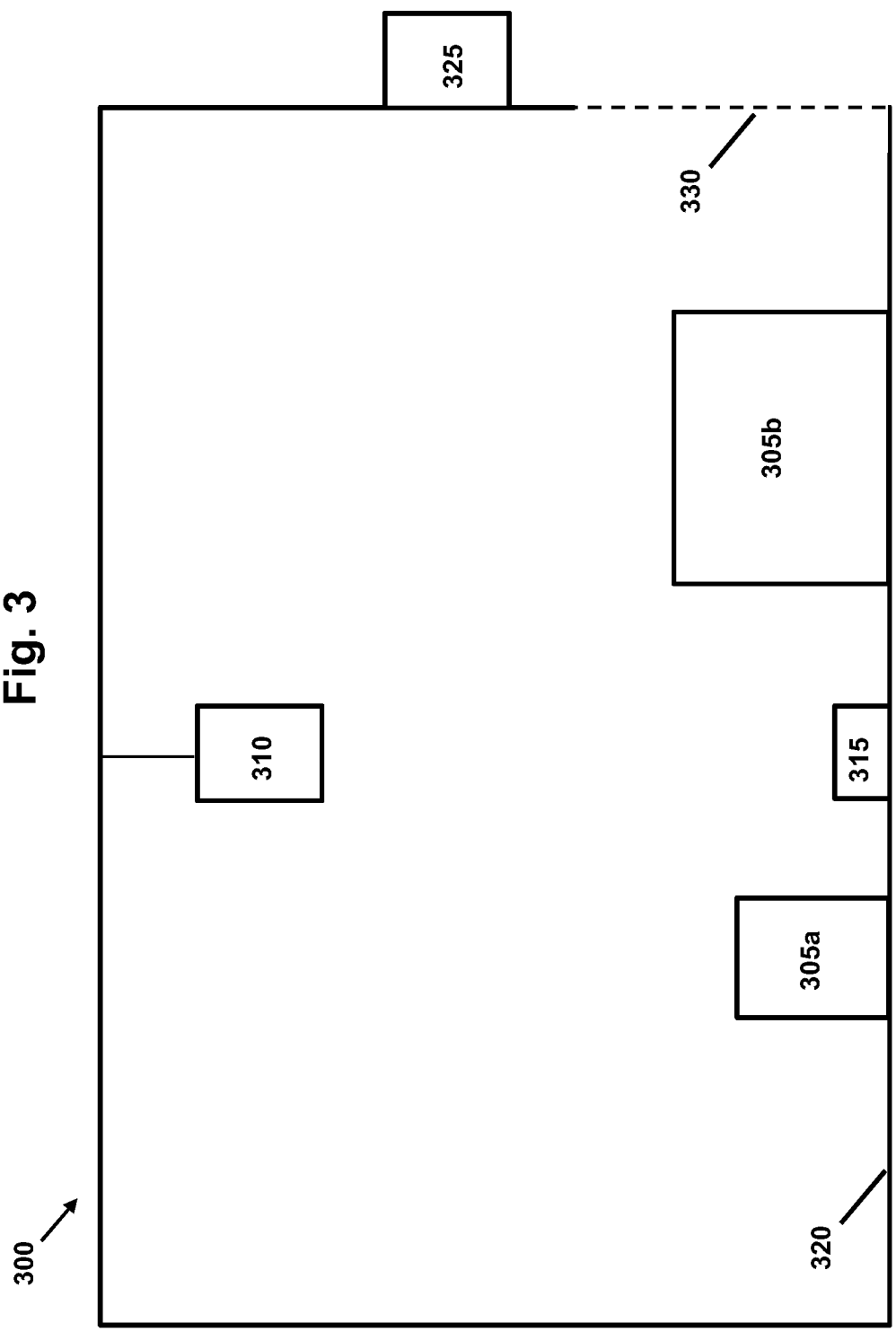
FIG. 3 shows the UV light monitoring system of FIG. 1 in use in a UV disinfection system.

FIG. 3 shows a UV light monitor as described above operating in the context of a UV disinfection system. A space 300 includes one or more objects 305a, 305b for disinfection. In the illustrated embodiment objects 305a, 305b are items of furniture but it will be appreciated that objects 305a, 305b can be any item that is to be disinfected including wall(s), a ceiling, a floor, etc.

A UV emitter 310 is present in space 300. In the illustrated embodiment UV emitter 310 is a fixed ceiling-mounted emitter. UV emitter 310 could alternatively be a mobile emitter that is capable of being movement within space 300. UV emitter 310 emits UV light, e.g. UV-A, UV-B and/or UV-C light. Although just one UV emitter is shown, multiple UV emitters can be present. A combination of fixed and mobile emitters is also contemplated.

UV emitter 310 can be any currently known or future developed device capable of emitting UV light. Such devices per se are known and so UV emitter 310 is not described in further detail here.

A UV light monitor 315 is provided within space 300. UV light monitor 315 is of the type described herein and can include any combination of the above-described features of UV light monitor 110. In the illustrated embodiment UV light monitor 315 is portable and is located on a floor 320 of space 300. This is purely exemplary and UV light monitor 315 can be located in any other position within space 300, e.g. on an upper surface of object 305a, 305b, on a wall of space 300 and/or in a corner of space 300. More than one UV light monitor like UV light monitor 315 can be provided in space 300. UV light monitor 315 and UV emitter 310 can be communicatively coupled with one another via a wired or wireless link that enables data and/or control instructions to be sent and received by one or both devices.

In the illustrated embodiment emitter 310 and/or UV light monitor 315 are respectively communicatively coupled to controller 325 via a wired and/or wireless connection. This is optional and in some embodiments controller 325 is omitted. In such a case emitter 310 and UV light monitor 315 may be in communication with one another.

Controller 325 includes a processor and a memory for storing digital data, as well as a human interface device that enables a person to submit commands and read off information. The human interface device may be, for example, a touchscreen, or a display and keyboard. The memory may be any form of computer-readable memory, e.g. RAM, ROM, etc. The memory may be physically located as part of controller 325 or it may be remotely located, e.g. electronic data storage in the Cloud. Controller 325 may include communications hardware such as a cellular radio and/or WiFi antenna, and the like, to enable the controller to communicate with a remote data processing device such as a Cloud-based server in order to access information including any information described herein as 'stored in the memory' of the controller.

Controller 325 is configured to send control signals to UV emitter 310 and/or UV light monitor 315 for various purposes including adjusting the operation of emitter 310 and retrieving UV irradiance data from UV light monitor 315. Control signals include an ON command to cause emitter 310 to start producing UV light and an OFF command to cause emitter 310 to stop producing UV light. Controller 325 may also control other aspects of emitter 310, e.g. if the disinfection apparatus includes a safety casing that is opaque to UV light, controller 325 may send control signals to cause the casing to open and close.

In the illustrated embodiment controller 325 is wall mounted and located outside of space 300 next to an entrance 330 to space 100. Entrance 330 is shown as a dashed line in FIG. 3 and in this exemplary case takes the form of a door. Controller 325 does not have to be wall mounted and alternatively can be mounted or otherwise located proximate space 300. As a further alternative controller 325 can be a portable device, e.g. a tablet computer, laptop computer, mobile telephone, and the like with a software application installed for communication with emitter 310 and/or UV light monitor 315. Entrance 330 may include one or more sensors (not shown) capable of detecting people, e.g. motion sensors such as laser sensor(s), microwave sensor(s) and/or passive infrared (PIR) sensor(s). The sensor(s) may be coupled to controller 325, which may be configured to transmit an OFF command and/or a 'close casing' command to emitter 310 in the event that the sensor(s) detect entry or attempted entry by a person via entrance 330.

Controller 325 may include an access control mechanism that prevents unauthorised personnel from operating it. For example, controller 325 may include a biometric input mechanism such as an iris scanner and/or fingerprint reader and may be configured to lock the human interface device unless an authorised biometric reading is provided. Other forms of access control, e.g. password or PIN entry, are also possible. As a further example, a physical device that has access credentials stored on it may be required to gain access to controller 325, e.g. a key card such as a Near-Field Communication (NFC) key card, or key fob, and the like.

The system shown in FIG. 3 is capable of determining a disinfection cycle time for a target surface based on a UV irradiance as calculated for the target surface, e.g. a wall of space 300. The UV irradiance can be calculated in the manner discussed earlier in this specification, e.g. using equation [1] or [2]. Advantageously the determined disinfection cycle time can be tailored specifically to the estimated irradiance experienced by the target surface, avoiding the need to perform an overkill type disinfection cycle that is longer than necessary and which may cause excessive degradation to UV-sensitive materials in space 300.

Figure 4:
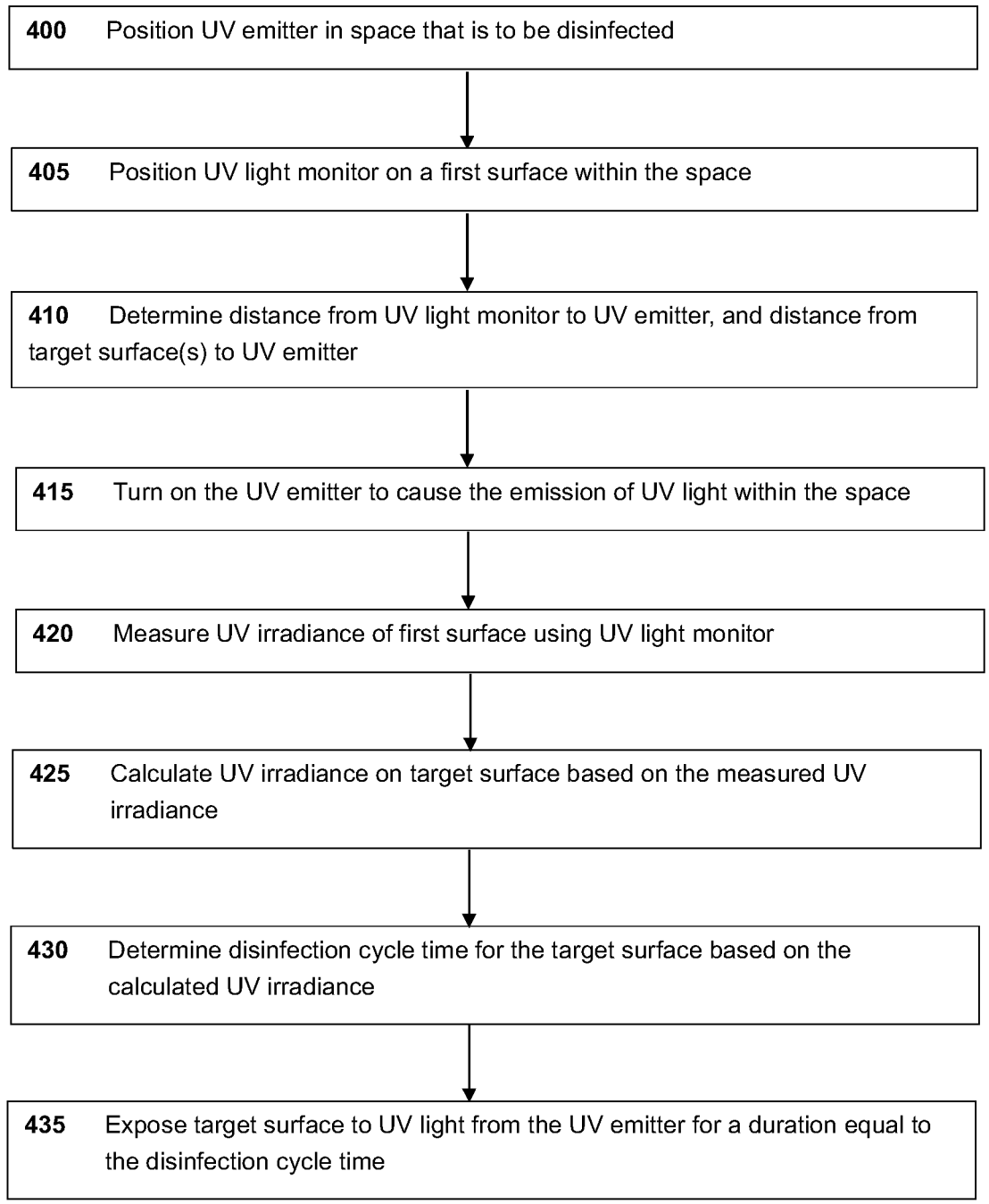
FIG. 4 is a flow diagram illustrating a process that can be performed by the UV disinfection system of FIG. 3.

The system of FIG. 3 can operate according to the process shown in FIG. 4. In step 400 a UV emitter in positioned in the space that is to be disinfected, e.g. space 300. The UV emitter may be UV emitter 310.

Following this in step 405 a UV light monitor is positioned on a first surface within the space, the first surface being different from the target surface. The UV light monitor may be UV light monitor 315. The first surface is not the target surface.

Optionally process 400 can include the step of measuring, with the UV light monitor, a background UV irradiance due to UV sources other than the emitter, e.g. the sun. The background irradiance can be subtracted from subsequent UV irradiance measurements made by the UV light monitor as described above in connection with equation [2].

In step 410, the distance from the UV light monitor to the UV emitter is determined. The distance from the or each target surface to the UV emitter is also determined. Any of the techniques for determining these distances set out above can be used.

In step 415, the UV emitter is activated, i.e. turned on, so as to cause the emitter to emit UV light in the space. In step 420 a UV irradiance of the first surface is measuring using the UV light monitor and in step 425 a UV irradiance on the target surface is calculated based on the UV irradiance measured in step 420. The UV irradiance on the target surface can be calculated by processor 105 according to any of the techniques discussed in this specification.

In step 430 the process determines a disinfection cycle time for the target surface based on the UV irradiance calculated in step 425. The disinfection cycle time can be calculated such that the target surface is exposed for an exposure time that provides a UV dose that is expected to disable or kill a target pathogen or set of target pathogens. This exposure time may be derived or obtained from a reference table, data sheet or other such source of information relating to the target pathogen or pathogens. For example, if pathogen X requires a dose of 10 $mJ/cm^2$ to achieve a log 4 kill level and the calculated irradiance is 0.01 $mW/cm^2$, the process time can be determined as 1000 seconds. Optionally an error margin can be built into the process time, e.g. a 5%, 10% or 15% addition to the calculated process time.

In step 435 the target surface is exposed to UV light from the UV emitter for a duration equal to the disinfection cycle time determined in step 430. This cycle time is tailored specifically for the target surface and therefore tends to enable target pathogen(s) to be disabled or killed to the desired reduction level without unnecessarily overexposing the target surface to UV light. This can advantageously return the space to its primary use rapidly and also minimise degradation of UV-sensitive materials within the space. Confidence in the required disinfection level being achieved may also be increased.

It is possible to define multiple target surfaces in a given space. In this case the process of FIG. 4 can be modified to repeat the target surface distance calculation of step 410 and steps 425 and 430 for each target surface. This will produce a data structure containing a set of target surfaces with their corresponding process times. The process time in this case can be set to the longest process time in the data structure to ensure that all target surfaces receive the necessary dose.

In the case where the UV light monitor includes a position alert component, the process of FIG. 4 can include the following additional steps: measuring a distance between the UV light monitor and a reference surface; and activating the position alert component in the case where a difference between the measured distance to the reference surface and a reference distance is greater than a threshold value. The position alert component may be of the type as described above. These additional steps can advantageously alert an operator to the case where the UV light monitor has not been correctly positioned. This can prevent misleading or otherwise unsuitable irradiance measurements being taken, which can in turn increase the accuracy of the UV irradiance calculated for the target surface. Additionally, UV light monitor placement is made simpler, enabling placement to be performed by operators that have not received special training.

In the case where the UV light monitor includes a solar cell and proximity alert component, the process of FIG. 4 can include the following additional steps: comparing a measured value for a parameter associated with the solar cell with a threshold value for the parameter; and activating the proximity alert component in the case where the measured value exceeds the threshold value. The parameter can be any of current, voltage and/or power associated with the solar cell as discussed above. The position alert component may be of the type as described above. These additional steps can advantageously alert an operator to the case where the UV light monitor has not been correctly positioned. This can prevent misleading or otherwise unsuitable irradiance measurements being taken, which can in turn increase the accuracy of the UV irradiance calculated for the target surface. Additionally, UV light monitor placement is made simpler, enabling placement to be performed by operators that have not received special training.

In the case where the UV light monitor includes first and second solar cells that are located on different faces of the UV light monitor and an orientation alert component, the process of FIG. 4 can include the following additional steps: determining a difference between a measured value for a parameter associated with the first solar cell with a measured value for the parameter associated with the second solar cell; and activating the orientation alert component in the event that the difference exceeds a threshold value. The orientation alert component may be of the type as described above. These additional steps can advantageously alert an operator to the case where the UV light monitor has not been correctly oriented. This can prevent misleading or otherwise unsuitable irradiance measurements being taken, which can in turn increase the accuracy of the UV irradiance calculated for the target surface. Additionally, UV light monitor placement is made simpler, enabling placement to be performed by operators that have not received special training. Moreover, the complexity of the UV light monitor is not significantly increased by the additional hardware and control instructions needed to provide the orientation information.

FIG. 5 shows a UV light monitoring system 500 according to another embodiment of the invention. Specifically, FIG. 5A shows a front view of the system and FIG. 5B shows a rear view of the system.

System 500 includes a processor 505 and a UV light monitor 510. The processor in the illustrated embodiment is embedded within UV light monitor 510 but this is not essential and alternatively the processor could be included as a separate component, e.g. as part of a process controller similar to, or the same as, process controller 325.

UV light monitor 510 includes a first solar cell 515 and a second solar cell 520. The first and second solar cells are located on different faces of UV light monitor 510. In the illustrated embodiment first solar cell 515 is located on a front face of UV light monitor 510 and second solar cell 520 is located on a rear face of UV light monitor 510, i.e. the first and second solar cells are located on opposite faces of the UV light monitor. This positioning, while preferred, is not essential and the first and second solar cells can be located on any faces of UV light monitor 510 so long as they are on different faces. Solar cells per se are known and so further details of the solar cells are not set out here. Preferably one of the solar cells is located on the same face of UV light monitor 510 as sensor 525 and the other of the solar cells is not located on the same face of UV light monitor as sensor 525.

UV light monitor 510 also including a UV sensor 525 that is capable of detecting UV light and generating a signal that is indicative of a UV irradiance incident on sensor 525. Sensor 525 is the same as sensor 120 described above.

UV light monitoring system 500 is configured to determine an orientation of the UV light monitor based upon a comparison between one or more parameters of the first solar cell and one or more parameters of the second solar cell. The parameters can be any one or more of voltage, current and/or power generated by the first solar cell and the second solar cell. Preferably the same parameter or combination of parameters is selected for each solar cell to enable direct comparison.

UV light monitoring system 500 is also configured to determine a UV irradiance incident upon a target surface based on measurements made by the UV sensor. The target surface in this embodiment can be the surface on which UV light monitor 510 is located. In this case the irradiance can be determined directly from the measurements made by sensor 525 because the assumption that the UV irradiance on sensor 525 is virtually identical to the UV irradiance on the target surface is valid in the case where the UV light monitor is positioned on the target surface.

Alternatively, the target surface can be a different surface to that which UV light monitor 510 is located on. In this latter case any of the aforementioned equations [1], [2], [3a] or [3b] can be used to calculate the irradiance on the target surface based on the measurements made by sensor 525.

The orientation as determined by the comparison can be used to determine whether UV light monitor 510 is correctly oriented to provide UV irradiance measurements that are usable to determine the UV irradiance on the target surface. For example, with the solar cells located as shown in FIG. 5, it is expected that first solar cell 515 would generate significantly more power than second solar cell 520 when UV light monitor 510 is correctly oriented. This is because in the correct orientation the face that incorporates sensor 520, and hence first solar cell 515, should be pointed directly towards the source of UV light (e.g. emitter 310). Second solar cell 520 is thus pointed directly away from the source of UV light by virtue of it being located on the opposite face to solar cell 515.

In the case where the UV light monitor is determined to be oriented sub-optimally, feedback can be provided to an operator. This may take the form of alerting the operator via an orientation alert component as discussed earlier in this specification.

A calibration may be performed where the difference in the selected parameter(s) may be mapped out for a range of orientations of UV light monitor 510 relative to a UV emitter. The data gathered in this calibration may be stored in a reference data table that is accessible to processor 505. This may enable processor 505 to determine the orientation of UV light monitor 510 by comparing the calculated difference with the reference data table. Feedback may be provided to an operator, e.g. 'monitor not correctly positioned', or 'rotate the UV light monitor approximately 90 degrees to the left'. Visual feedback may alternatively or additionally be provided, e.g. a graphic on a display screen indicating a direction through which the UV light monitor should be rotated.

In some cases UV light monitor 510 may be capable of adjusting its orientation without intervention from an operator. For example, UV light monitor 510 may include wheels and a motor, or some other system that enables it to undergo motion. In this case UV light monitor 510 may adjust its position until the difference in the parameter or parameters for the first and second solar cells is equal to a value that indicates optimal positioning, or within a tolerance or range of this value.

Many modifications and variations to the specifics of the invention will be apparent to a person skilled in the art having the benefit of the present disclosure. All such modifications and variations are also embodiments of the invention.

What is claimed is:

1. A system for disinfecting a space, comprising:
a system comprising a UV light monitor including a UV sensor, and a controller including a processor operable to respond to computer-readable instructions stored in a memory to:
calculate a UV irradiance on a target surface that is remote from the UV light monitor based on: UV light intensity measurements made by the UV light monitor, a first angle between the UV sensor and UV light that is generated by a UV emitter and is incident on the UV sensor; a second angle between the target surface and UV light generated by the UV emitter that is incident on the target surface; a distance between the UV emitter and the UV sensor; and a distance between the UV emitter and the target surface, and
determine a disinfection cycle time for the target surface based on the calculated UV irradiance; the system for disinfecting a space further comprising;
a UV emitter, wherein the controller is operable to respond to computer-readable instructions stored in the memory that cause the UV emitter to expose the target surface to UV light for a duration equal to the disinfection cycle time.

2. The system for disinfecting a space of claim 1, wherein the first and second angles are different.

3. The system for disinfecting a space of claim 1, wherein the UV light sensor is configured to detect UV light incident on the sensor across a range of angles and to output a UV intensity as a function of incidence angle.

4. The system for disinfecting a space of claim 1, wherein the UV light monitor further includes a distance measuring component that is configured to measure a distance from the UV light monitor to the UV emitter.

5. The system for disinfecting a space of claim 1, wherein the UV monitor includes a position alert component and a reference distance measuring component configured to measure a distance to a reference surface, and wherein the UV light monitoring system is configured to activate the position alert component in the case where a difference between the measured distance and a reference distance is greater than a threshold value.

6. The system for disinfecting a space of claim 1, wherein the UV light monitor includes a solar cell and a proximity alert component, and wherein the UV light monitor is configured to activate the proximity alert component based upon a parameter relating to the solar cell exceeding a threshold value.

7. The system for disinfecting a space of claim 6, wherein the parameter relating to the solar cell is one or more of: a voltage generated by the solar cell, a current generated by the solar cell, and a power generated by the solar cell.

8. The system for disinfecting a space of claim 1, wherein the UV light monitor includes at least first and second solar cells that are located on different faces of the UV light monitor, and wherein the system is configured to determine an orientation of the UV light monitor based upon a comparison between a parameter of the first solar cell and a parameter of the second solar cell.

9. The system for disinfecting a space of claim 8, wherein the faces of the UV light monitor are opposite one another.

10. The system for disinfecting a space of claim 8, wherein the parameter of the first solar cell and the parameter of the second solar cell are both one or more of the following: a voltage, a current and a power.

11. The system for disinfecting a space of claim 8, wherein the UV light monitor further includes an orientation alert component and wherein the UV light monitor is configured to activate the orientation alert component based upon a comparison between the determined orientation and a reference orientation.

12. The system for disinfecting a space of claim 1, wherein the target surface is any of: a wall, a ceiling, a corner of a room, and/or a face of an item of furniture.

13. The system for disinfecting a space of claim 1, wherein the processor is located within the UV light monitor.

14. The system for disinfecting a space of claim 1, wherein the processor is located within a control unit that is in wireless communication with the UV light monitor.

15. The system for disinfecting a space of claim 1, wherein the UV light monitor is portable.

16. The system for disinfecting a space of claim 1, further comprising one or more additional UV light monitors each having a respective UV sensor, wherein the system is configured to calculate one or more additional UV irradiance on the target surface based on UV light intensity measurements made by the one or more additional UV light monitors, wherein each of the one or more additional UV light monitors are remote from the target surface.

17. The system for disinfecting a space of claim 1, wherein the UV emitter comprises one or more fixed units mounted on a wall or ceiling of a space that includes the target surface and/or one or more mobile units that are capable of motion within a space that includes the target surface.

18. The system for disinfecting a space of claim 1, wherein the UV emitter is configured to emit any combination of: UV-A radiation, UV-B radiation and/or UV-C radiation.

\* \* \* \* \*